United States Patent [19]

Neurath

[11] Patent Number: 4,459,359

[45] Date of Patent: Jul. 10, 1984

[54] SENSITIVE IMMUNOASSAYS OF ANTIGENS OR ANTIBODIES SEQUESTERED WITHIN IMMUNE COMPLEXES

[75] Inventor: A. Robert Neurath, New York, N.Y.

[73] Assignee: New York Blood Center, Inc., New York, N.Y.

[21] Appl. No.: 323,003

[22] Filed: Nov. 19, 1981

[51] Int. Cl.$^3$ .................... G01N 33/54; G01N 33/56
[52] U.S. Cl. .................... 436/507; 436/530; 436/531; 436/804; 436/825; 436/828; 435/4; 435/7
[58] Field of Search .......... 424/1, 1.1, 85, 86, 424/177, 153; 436/506–509, 518–535, 536, 539, 540–543, 804, 811, 820, 823, 824, 828, 18, 174, 177, 178, 825; 435/4, 7, 21, 25, 28; 23/915, 920

[56] References Cited

U.S. PATENT DOCUMENTS 3,872,225  3/1975  Coller et al. ............................ 424/1
4,138,213  2/1979  Masson et al. .......................... 424/1

OTHER PUBLICATIONS

Paganelli, R. et al., Clinical Experimental Immunology, vol. 46, pp. 44–53 (10–1981).
Jones, V. E. et al., J. Immun. Method, vol. 44, pp. 249–278, (1981), p. 3 spec.

Primary Examiner—Benjamin R. Padgett
Assistant Examiner—M. Moskowitz
Attorney, Agent, or Firm—Sprung, Horn, Kramer & Woods

[57] ABSTRACT

A process for determining the presence of an antigen or antibody in a sample wherein said antigen or antibody exists in the form of an immune complex which comprises:

A. contacting the immune complex originating from the sample suspected of containing immune complex with a dissociating buffer whereby said immune complex, if present, is dissociated into antigen and antibody;
B. contacting a solid support which binds proteins with said dissociating buffer suspected of containing antigen or antibody and removing said buffer;
C. washing said solid support;
D. adding protein to fill unoccupied sites on said solid support;
E. adding radioactively labeled or enzyme labeled antibody or antigen to said solid support, said labeled antibody or antigen corresponding to antigen or antibody on said solid support, incubating the resultant mass and washing the same;
F. measuring the radioactivity or enzymatic activity associated with the solid support.

23 Claims, 2 Drawing Figures

FIG. I.

SENSITIVE IMMUNOASSAYS OF ANTIGENS OR ANTIBODIES SEQUESTERED WITHIN IMMUNE COMPLEXES

BACKGROUND OF THE INVENTION

1. Field of the Invention

This invention relates to a process for determining the presence of a given antigen or antibody in a serum. More especially, this invention relates to a process for determining the presence of an antigen or antibody in a sample containing such antigen or antibody in the form of an immune complex. This invention is particularly concerned with determining the presence of antigen or antibody in a sample wherein said antigen or antibody exists in the form of an immune complex in small quantities (range pg to mg/ml).

2. Discussion of Prior Art

Immune complexes play a pathogenic role in many infectious, auto-immune and neoplastic diseases. (E. V. Barnett, D. W. Knutson, C. K. Abras, D. S. Chia, L. S. Young, M. R. Liebling; *Circulating Immune Complexes; Their Immunochemistry, Detection, And Importance,* ANN. INTERN. MED. 91, 430–440, 1979; J. L. Dienstag, A. K. Bhan, H. J. Alter, S. J. Feinstone, R. H. Purcell; *Circulating Immune Complexes In Non-A, Non-B Hepatitis,* LANCET 1, 1265–1267, 1979, J. R. Wands, E. Mann, E. Alpert: *The Pathogenesis Of Arthritis, Associated With Acute Hepatitis B Surface Antigen-Positive Hepatitis: Complement Activation And Characterization Of Circulating Immune Complexes,* J. CLIN. INVEST. 55, 930–936, 1975; V. E. Jones, E. Orlans: *Isolation Of Immune Complexes And Characterization Of Their Constituent Antigens And Antibodies In Some Human Diseases: A Review,* J. IMMUNOL. METHODS 44, 249–270 1981; R. C. Williams, Jr.: *Immune Complexes In Human Diseases,* ANN. REV. MED. 32, 13–28, 1981). Antigens corresponding to infectious agents, self-antigens and tumor antigens, respectively, may not be present in biological fluids in free form but only complexed with antibodies. Therefore, they may elude detection unless methods for isolation of the respective antigens from antibodies are developed. Although such separation techniques have been described (A. B. Pereira, A. N. Theofilipoulos, F. J. Dixon: *Detection And Partial Characterization Of Circulating Immune Complexes With Solid Phase Anti-C3,* J. IMMUNOL. 125, 763–770, 1980; R. Heimer, D. L. Glick, J. L. Abruzzo: *The Detection Of Antigens In Immune Complexes;* SCAND. J. IMMUNOL. 13, 441–446, 1981; V. E. Jones, E. Orlans: *Isolation Of Immune Complexes And Characterization Of Their Constituent Antigens And Antibodies In Some Human Diseases: A Review,* J. IMMUNOL. METHODS, 44, 249–278, 1981) they are useless from a practical point of view if many specimens need to be analyzed.

Although successful attempts to identify antigens within immune complexes without separating them from antibodies have been described, (R. Heimer, D. L. Glick, J. L. Abruzzo: *The Detection Of Antigens In Immune Complexes,* SCAND. J. IMMUNOL. 13, 441–446, 1981; V. E. Jones, E. Orlans: *Isolation Of Immune Complexes And Characterisation Of Their Constituent Antigens And Antibodies In Some Human Diseases: A Review,* J. IMMUNOL. METHODS, 44, 249–278, 1981; S. Husby, S. E. Svehag, H. Nielsen, N. Hiby, P. O. Schitz: *Methodological Approaches To Antigen Identification In Soluble Immune Complexes; A Model Study,* ACTA. PATH. MICROBIOL. SCAND. 89C, 255–260; C. Cunningham-Rundles: *The Identification Of Specific Antigen In Circulating Immune Complexes By An Enzyme-Linked Immunosorbent Assay: Detection Of Bovine-χ-Casein IgG Complexes In Human Sera,* EUR. J. IMMUNOL. 11, 504–509, 1981) such successes appear to be an exception and are generally not applicable for diagnostic purposes. Immune complexes containing infectious agents may retain infectivity and may thus become involved in the transmission of disease. Furthermore, circulating immune complexes may be involved in unfavorable modulation of the immune response leading to perpetuation of the disease. Therefore, the detection of medically significant antigens sequestered within immune complexes appears to be of great importance, and a necessary addition to many sensitive immunoassays which have been utilized in medical diagnosis during recent years.

It is an object of this invention, therefore, to provide a process for the detection of given antibodies or antigens in a sample where the antigens or antibodies are present in the form of an immune complex. It is especially desirable to provide a process whereby such antibodies or antigens can be detected in said samples even present in the form of an immune complex in concentrations less than 1 nanogram per milliliter.

SUMMARY OF THE INVENTION

These and other objects of the invention are provided by a process for determining the presence of an antigen or antibody in a sample wherein such antigen or antibody exists in the form of an immune complex which process comprises:

A. contacting the immune complex originating from the sample with a dissociating buffer whereby said immune complex, if present, is dissociated into antigen and antibody;

B. removing said dissociating buffer suspected of containing dissociated antigen and antibody;

C. contacting a solid support which binds proteins with said dissociating buffer suspected of containing antigen or antibody and removing said buffer;

D. washing said solid support;

E. adding protein to fill unoccupied sites on said solid support;

F. adding radioactively labeled or enzyme labeled antibody or antigen to said solid support, incubating the resultant mass and washing the same;

G. measuring the radioactivity or enzymatic activity associated with the solid support Preferably, especially for detection of antigen or antibody in low concentrations, the sample containing the immune complex is contacted with an immune complex precipitating agent, e.g., polyethylene glycol of molecular weight 600 to 100,000, the precipitate is separated from the supernatant material and the immune complex is taken up in a dissolved form by contacting the same with a neutral, preferably non-dissociating, buffer (pH 6 to 8). That liquid is then applied to a solid support having immune complex binding sites whereby if the immune complex is present it becomes bound to such site. That solid support is recovered and washed and the dissociating buffer, according to step A, is added thereto to remove the immune complex and dissociate it into antigen and antibody.

DESCRIPTION OF SPECIFIC EMBODIMENTS

In carrying out a preferred embodiment of the process, the first step involves the isolation of the immune complex from other components with which it is in admixture, normally other proteins. In particular, the first step involves the removal of these immune complexes from sera in which they are present by methods generally known in the art. According to a preferred embodiment of the invention, the immune complexes are adsorbed onto a solid support or otherwise precipitated from the serum containing the same. This can be effected by precipitation with polyethylene glycol and subsequent adsorption of the immune complex on a support which adsorbs immune complexes and does not adsorb protein other than immunoglobulin, by using Staphylococci carrying protein A or by the use of protein A linked to a solid support such as agarose. Alternatively, one can use conglutinin linked to a solid support as adsorbent for the immune complex. Other alternatives include the use of complement component CIq linked to a solid support or an antibody to an immunoglobulin linked to a solid support. Furthermore, one can use an antibody to an appropriate complement component linked to a solid support or cells bearing receptors for antibody or complement components of immune complexes. The isolation of the immune complex can be performed by any of the methods heretofore known, including those methods disclosed in the following publications:

E. V. Barnett, D. W. Knutson, C. K. Abras, D. S. Chia, L. S. Young, M. R. Liebling; *Circulating Immune Complexes; Their Immunochemistry, Detection, And Importance*, ANN. INTERN. MED. 91, 430–440, 1979.

M. P. Davey, L. Korngold; *A Solid-Phase Assay For Circulating Immune Complexes Using Monoclonal Rheumatoid Factors And Peroxidase-Linked Protein A*, J. IMMUNOL. METHODS, 44, 87–100, 1981.

A. Gabriel, Jr., V. Angello: *Detection Of Immune Complexes. The Use Of Radioimmunoassays With CIq And Monoclonal Rheumatoid Factor*, J. CLIN. INVEST. 59, 990–1001, 1977.

A. B. Pereira, A. N. Theofilopoulos, F. J. Dixon: *Detection And Partial Characterization Of Circulating Immune Complexes With Solid Phase Anti C3*, J. IMMUNOL. 125, 763–770, 1980.

P. Casali, P.-H. Lambert: *Purification Of Soluble Immune Complexes From Serum Using Polymethylmethacrylate Beads Coated With Conglutinin Or CIq*, CLIN. EXP. IMMUNOL. 37, 295–309, 1979.

R. Heimer, D. L. Glick, J. L. Abruzzo: *The Detection Of Antigens In Immune Complexes*, SCAND. J. IMMUNOL., 13, 441–446, 1981.

V. E. Jones, E. Orlans: *Isolation Of Immune Complexes And Characterisation Of Their Constituent Antigens And Antibodies In Some Human Diseases: A Review*, J. IMMUNOL. METHODS, 44, 249–278, 1981.

R. C. Williams, Jr., *Immune Complexes In Human Diseases*, ANN. REV. MED. 32, 13–28, 1981.

The disclosures of these publications are hereby incorporated herein by reference.

After effecting adsorption of the immune complex onto a solid support, the serum is removed therefrom, and the solid support is washed to remove excess proteins.

The washing is followed by dissociation of the antigens or antibodies, originating from the immune complexes, from the solid support. To achieve this, the solid support containing the immune complex is contacted with a dissociating buffer which removes the immune complex from the solid support and dissociates it into its antigen and antibody components. To achieve this dissociating buffers are employed such as urea, guanidine hydrochloride, thiocyanate salts such as sodium and potassium thiocyanate, $MgCl_2$, lithium diiodosalicylate or solutions of low (2–3.5) or high (10–11.5) pH. Particular contemplated solutions of low pH are aqueous solutions of: glycine-hydrochloric acid, citric acid-citrate, acetic acid, propionic acid and the like.

Particular contemplated solutions of high pH are those aqueous solutions of the following alkaline materials: sodium carbonate-bicarbonate; sodium borate; tris (hydroxymethyl) aminomethane and the like.

Other buffers which can be used for this purpose include: buffers containing salts of lithium (lithium thiocyanate), buffers containing iodides (sodium, potassium, lithium, iodide) buffers containing ammonium compounds such as ammonium hydroxide, ammonium chloride and the like.

It is preferred to use as the buffer an aqueous solution of an alkali or alkaline earth metal thiocyanate whose pH is 6–8. Such solution can contain minor amounts of other buffer components or can be free of other buffer components. Generally, such solutions more effectively dissociate the immune complex than those buffers of low pH (2–3.5) or high pH (10–11.5). These preferred buffers are effective due to the salt components themselves rather than the extent to which hydrogen or hydroxyl ions are present.

It is important that the buffer be one which substantially completely dissociates the immune complex from the solid support and dissociates the immune complex itself into its component antigen and antibody.

Alternatively, one can proceed by contacting the immune complex originating from the sample with a dissociating buffer and thereby dissociating the immune complex without initially adsorbing it onto a solid support.

Dissociation of the immune complex is generally carried out at a temperature of between 1° and 45° C., preferably room temperature. Dissociation is preferably effected by contacting the immune complex, for example adsorbed onto the solid sorbent, with the dissociating buffer for at least 2 minutes, preferably at least 5 minutes and generally between 5 and 30 minutes. Thereafter, the solid support, substantially free of immune complex, is separated from the dissociating buffer which is now suspected of containing antigen or antibody derived from immune complex contained in the original sample.

The dissociating buffer suspected of containing antigen or antibody is thereafter brought in contact with a solid support which binds proteins. For this purpose, a wide variety of solid supports can be used. For this purpose, one can employ for instance, a paper-type material which has been treated with a protein binding agent such as diazobenzyloxy methyl paper or diazophenylthioether paper. Treatment of paper with these agents renders the paper capable of binding proteins. Alternatively, one can use a nitrocellulose sheet or similar material. In particular, it is contemplated to use as the solid sorbent a plastic material such as polystyrene, a polyvinyl, e.g., polyvinyl chloride, polyvinylidene chloride, polyacrylonitrile, polyvinylacetate.

Other plastics which can be used include polyethylene, polypropylene, nylon, and derivatized glass.

Quite surprisingly, when these and other protein sorbing solid supports are brought in contact with the dissociating buffer suspected of containing the antigen or antibody derived from the immune complex, irreversible attachment of the proteins is effected, notwithstanding the copresence of those components in the dissociating buffer which dissociated the antigen and antibody and served to remove the immune complex from the solid support. In particular, it has been quite surprisingly observed that antigen or antibody proteins in a dissociating buffer attach to a wide variety of solid matrices and in such environment the presence of the dissociating buffers does not minimize attachment of the protein to the solid matrices, nor does it cause elution of proteins which had been adsorbed to such matrices.

By effecting adsorption of antigen or antibody derived from immune complex on the solid support, the existence of antibody or antigen can be determined by a simple radioimmunoassay or enzyme labeled immunoassay technique.

Generally speaking, the solid support is treated with the dissociating buffer suspected of containing antigen or antibody at a temperature of between 0° and 45° C., preferably between 15° and 25° C. for at least 60 minutes, preferably at least 2 hours and generally overnight, all to insure maximum adsorption of antigen and antibody, separately from one another, onto the solid support. It should be noted that for this adsorption, it is unnecessary that the solid sorbent be pretreated with a protein binding agent. After the solid sorbent is treated with the dissociating buffer containing antibody or antigen, the solid support is washed free of extraneous material.

Thereafter, those sites on the solid sorbent not occupied by antigen or antibody are filled with protein so that substantially all of the available sites on the solid support are occupied. This insures that upon subsequent addition of a radioactively labeled or enzyme labeled antibody or antigen, reaction occurs upon the predeposited antigen or antibody derived from the original immune complex, so that detection of the presence of such radioactive labeled or enzyme labeled material accurately detects the extent to which antigen or antibody derived from the original immune complex is present on the solid support.

To this end, one can use a wide variety of materials to occupy the unoccupied binding sites on the solid support. These include, in particular, proteins. It is particularly contemplated to use the following materials as binding site occupiers: bovine serum albumin, gelatine, normal human serum or animal sera (bovine, calf, fetal calf, chicken, etc.) Preferably, the solid support is incubated with a solution of bovine serum albumin to saturate the unoccupied protein binding sites.

Thereafter, the sample is washed free of extraneous material, and there is added radioactively labeled or enzyme labeled antibody or antigen corresponding to the antigen or antibody suspected of being bound to the solid support. Thus, if one is desirous of determining the presence of a given antigen on a solid support, one adds a radioactively labeled or enzyme labeled antibody thereto. Similarly, if one is desirous of determining the presence of a given antibody on the solid support, one adds a radioactive or enzyme labeled antigen thereto. In either case, the antibody or antigen added is incubated with the antigen or antibody on the solid support. Thereafter, the composition is washed free of extraneous material and the solid support is tested for radioactivity or enzymatic activity.

By the technique of the invention, sub-nanogram quantities of antigen or antibody can be detected from samples containing antigen or antibody in the form of an immune complex. The process does not require the disposition of purified antibody or antigen on a solid support. In other words, one does not have to and cannot use as reagent a solid support to which has been bound purified antibody or antigen corresponding to the antigen or antibody to be detected in a given sample.

In carrying out the invention one can use as the solid support a paper which has been treated with a reagent which will render the paper capable of binding proteins. The following activated papers rendered capable of binding proteins are particularly contemplated: diazobenzyloxymethyl paper and diazophenylthioether paper. These are commercially available, for example, from Schleicher and Schuel, Keene, N.H.

Generally speaking, when working with these papers or other papers such a nitrocellulose sheets, it is desirable following contact of the papers with the dissociating buffer containing antigen or antibody to fill the sites with a protein binding site occupier such as provided by bovine serum albumin. This step usually precedes contact of the solid support with the radioactively labeled or enzyme labeled antibody or antigen. However, when one uses a plastic material for such purpose, it is unnecessary to pretreat the plastic with a protein site adsorber prior to contact with the radioactive or enzyme labeled antigen or antibody. Rather, instead of such pretreatment one can use a mixture of protein site adsorbers and radioactive or enzyme labeled antigen or antibody. Under such circumstances, the antigen or antibody on the solid support preferentially combines with the radioactive or enzyme labeled antibody or antigen leaving the protein site adsorber to preferentially bind with the unoccupied sites on the solid support.

The incubation steps required in carrying out the invention can be effected in known manner, such as by incubating antigen with labeled antibody at temperatures of 37° to 50° C. for 1–8 hours or at 18° to 30° C. for 16 to 72 hours.

Washings are typically effected using an aqueous solution such as one buffered at a pH of 6–8, preferably at a pH of about 7, employing an isotonic saline solution.

The sensitivity of the procedure is improved if following adsorption of the immune complex onto a separating support, excess antibody which may have also become bound to the immune complex binding sites thereon, are removed. For instance, in the detection of antigens in the form of immune complexes where it is suspected that the serum contains large quantities of free antibody, the sensitivity of the technique is improved if that free antibody, which together with the immune complex becomes bound to the binding sites on the separating support and thereafter dissociated by contact with the dissociating buffer, is removed from the dissociating buffer prior to contact of the dissociating buffer with the solid support in accordance with step C. Separation of excess antibodies from antigen can be achieved by ion exchange chromatography in solutions containing 6–8M urea. Ion exchange can be performed using DEAE cellulose, CM-cellulose or similar derivatives of Sephadex or Agarose. It should be understood that removal of these free antibodies, is not required to carry out the process. It simply improves the sensitivity of the overall technique.

The process of the invention is effected notwithstanding the copresence of other proteins, as will appear from the examples below.

BRIEF DESCRIPTION OF DRAWINGS

Referring to the drawings herein.

Figure 1:
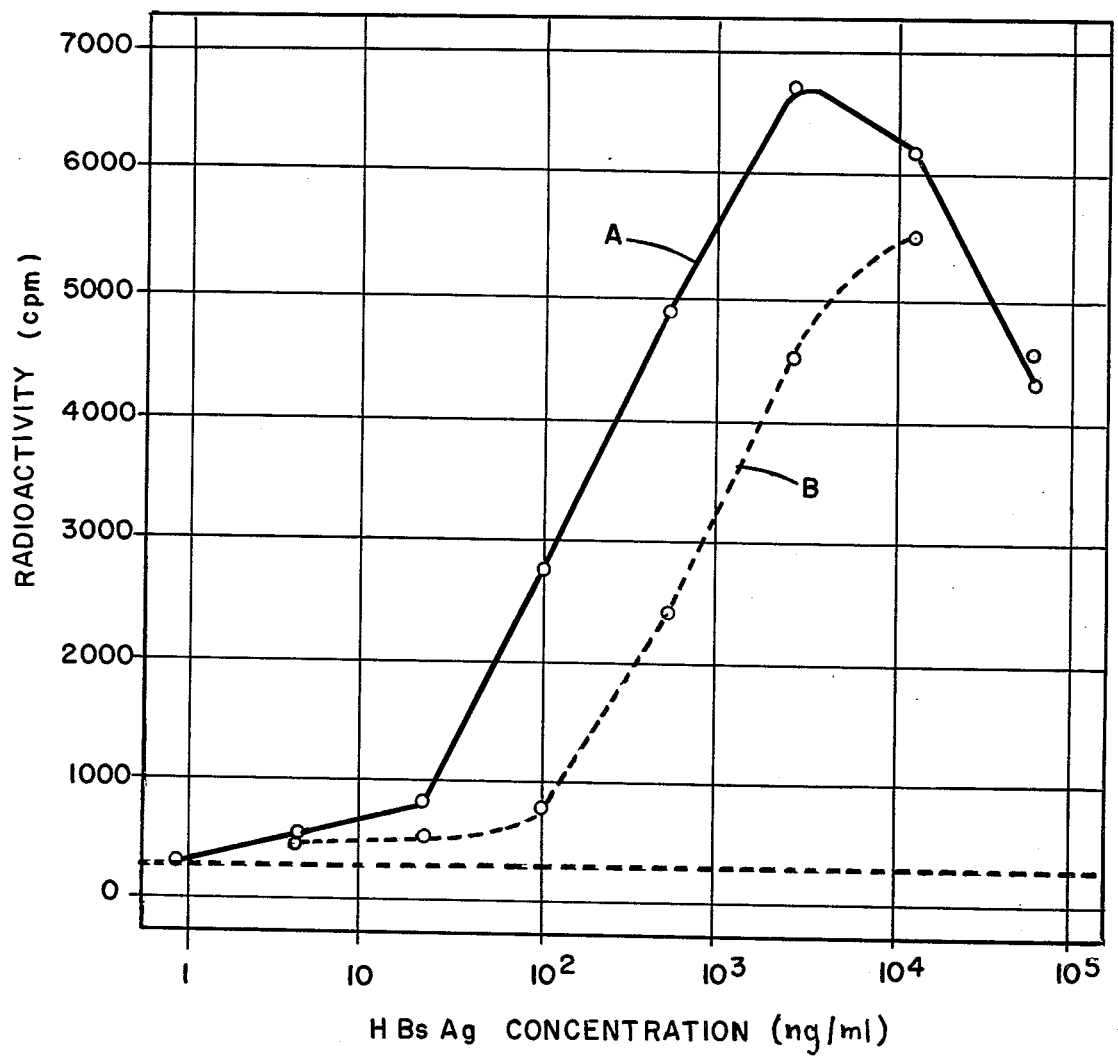
FIG. 1 is a graph showing the sensitivity of the technique of the invention in the detection of the presence of hepatitis B surface antigen in the absence of and in the presence of another protein.

The process of the invention is useful in the detection of virtually all antigens or antibodies sequestered within immune complexes. It is useful in the detection of the following antigens when present in the forms of immune complexes: hapatitis B surface antigen, histocompatability antigens, influenza hemaglutinin, fowl plague virus hemaglutinin, infectious ectromelia virus antigens, fowl pox virus antigens, *herpes simplex* virus antigens, infectious bovine Rhinotracheitis virus antigens, equine Rhinopneumonitis virus antigens, malignant catarrh virus antigens of cattle, as well as antigens of the following viruses: vaccinia, Epstein-Barr virus, polio, rubella, cytomegalovirus, smallpox, *herpes simplex* types I and II, yellow fever and many others including: Marek's disease virus, Sheep pulmonary adenomatosis virus, Feline panleucopaenia virus, Mink enteritis virus, African horse sickness virus, Blue tongue virus, Infectious pancreatic necrosis virus of trout, Fowl sarcoma virus, Avian leukosis viruses, Newcastle disease virus, Parainfluenza virus 1, Parainfluenza virus 2, Parainfluenza 3, Parainfluenza virus 4, Mumps virus, Canine distemper virus, Measles virus, Respiratory syncytial virus, Myxovirus, Type A viruses such as Human influenza viruses, e.g., Ao/PR8/34, A1/CAM/46, and A2/Singapore/1/57; Fowl plague virus; Type B viruses e.g., B/Lee/40; Rabies virus, Eastern equine encephalitis virus; Venezuelan equine encephalitis virus; Western equine encephalitis virus; Yellow fever firus, Dengue type 1 virus, Dengue type 2 virus; Dengue type 3 virus; Dengue type 4 virus; Japanese encephalitis virus, Kyasanur Forest virus; Louping ill virus; Murray Valley encephalitis virus; Omsk haemorrhagic fever virus (types I and II); St. Louis encephalitis virus; Human rhinoviruses, Foot-and-mouth disease virus; Poliovirus type 1, 2 and 3; Avian infectious bronchitis virus; Human respiratory virus; Transmissible gastro-enteritis virus of swine; Lymphocytic choriomeningitis virus; Lassa virus; Machupo virus; Pichinde virus; Tacaribe virus; Papillomavirus, Hapatitis A, *Varicella zoster.*

It can also be used for detection of antigens of parasites and bacteria such as: organisms carrying malaria (*P. Falciparum, P. Ovace,* etc.), Schistosomiasis, Onchocerca, Volvulus and other filarial parasites, Trypanosomes, Leishmania, Chagas disease, ameobiasis, hookworm, and the like; leprosy, tuberculosis, syphilis, gonorrhea and so forth.

Of course, the process is also useful in the detection of the corresponding antibodies when bound in the form of an immune complex.

In order to more fully illustrate the invention and the manner of practicing the same, the following examples are presented.

EXAMPLE 1

In order to determine whether solid supports containing protein binding sites bind antigens or antibodies in dissociating or non-dissociating buffers, various levels of hepatitis B surface antigen (HBsAg) in either phosphate buffered saline (pH 7.2) or in 8 molar urea-0.01 molar phosphate (pH 8.0) or in 3 molar sodium thiocyanate solutions were blotted onto nitrocellulose paper sheets. Five microliters of each solution were blotted. The nitrocellulose was incubated with a solution of bovine serum albumin to saturate the unoccupied protein binding sites.

Subsequently, the so-treated nitrocellulose was incubated with $^{125}$I-labeled anti HBsAg antibodies extensively, washed to remove excess labeled antibody and subitted to autoradiography.

The test strips reflected that in each instance the HBsAg was bound to the protein binding sites of the nitrocellulose paper. Thus, HBsAg antigen was bound to the paper when present in a dissociating buffer (8 molar urea or sodium thiocyanate solution) or in a non-dissociating buffer (phosphate buffered saline). The test further revealed that HBsAg could be detected at levels of down to a low as $10^{-1}$ nanograms. The tests were particularly sensitive at the $10^0$–$10^4$ nanogram HBsAg concentration.

EXAMPLE 2

In order to determine whether antigens become attached to surfaces of plastic when dissolved in dissociating buffers, so as to be detectable subsequently by the use of labeled antibodies, purified hepatitis B surface antigen (HBsAg) was serially diluted in 3 molar sodium thiocyanate. Polystyrene beads were added to each dilution. The mixtures were incubated overnight at room temperature. The beads were washed, incubated with $^{125}$I-labeled antibodies in a solution of 5 percent bovine serum albumin for 1 hour at 45° C., washed and counted in a gamma counter. The results are graphically depicted in FIG. 1, curve A.

When excess of another protein was added to each of the dilutions of HBsAg in 3 molar sodium thiocyanate (400 mg/ml of IgG), HBsAg could still be detected (curve B), although the sensitivity of detection was somewhat diminished.

This indicates that contamination of immune complexes of a particular antigen of interest with other immune complexes or other protein contaminants does not prevent the antigen detection. Similar results were obtained with antigens other than HBsAg, indicating that the described method is universal.

EXAMPLE 3

Detection of HBsAg Sequestered with Immune Complexes

Figure 2:
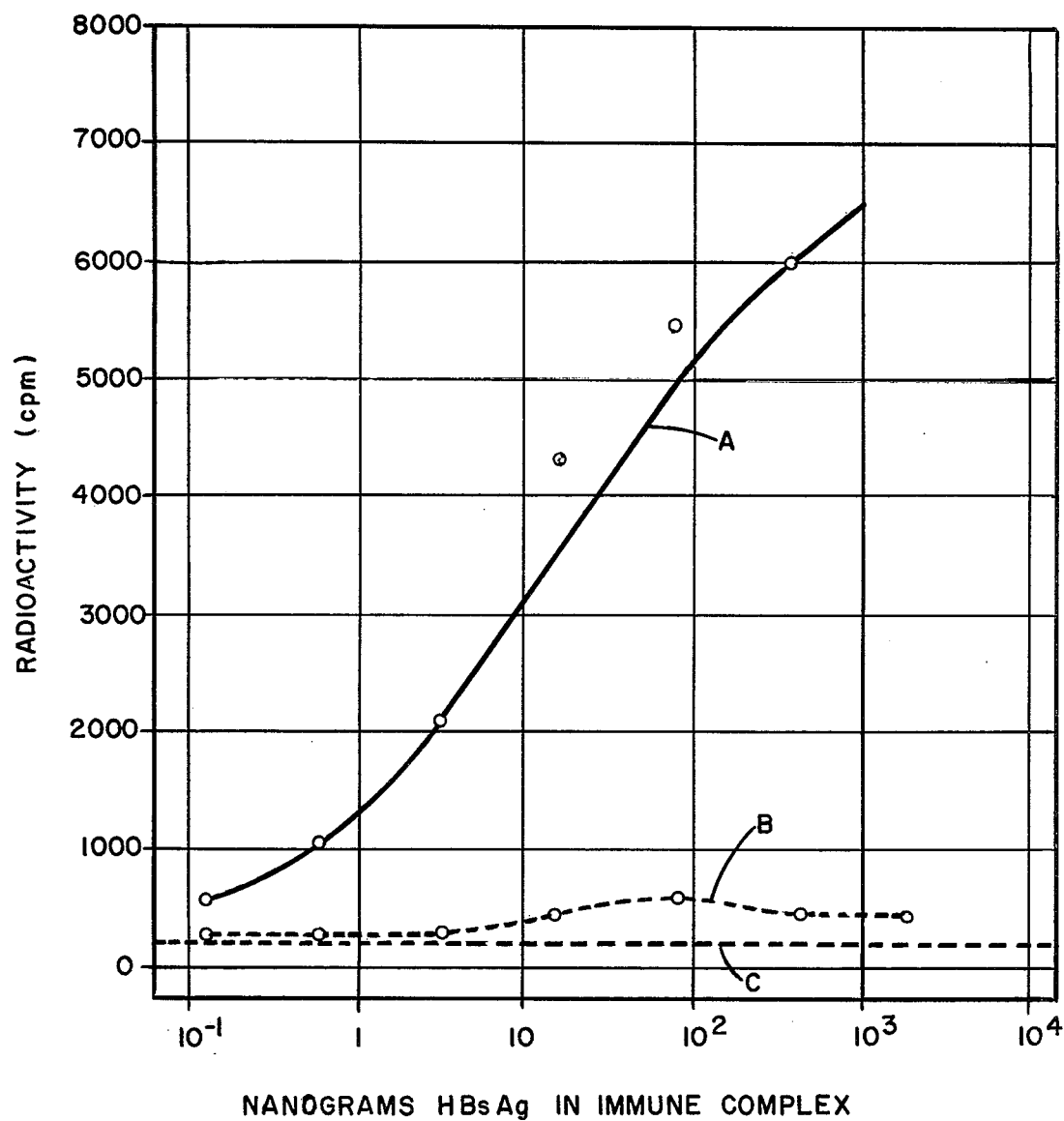
FIG. 2 is a graph showing the high sensitivity of the process in detecting hepatitis B (surface) antigen in an immune complex. This figure further shows the very low sensitivity of the process if a non-dissociating buffer is employed.

Immune complexes containing known quantities of HBsAg were serially diluted in 3 molar sodium thiocyanate or in phosphate buffered saline (pH 7.2). Polystyrene beads were added to each dilution. After overnight incubation at room temperature, the beads were washed, mixed with $^{125}$I-labeled antibodies in a solution containing 5 percent bovine serum albumin, incubated 1 hour at 45° C., washed and counted in a gamma counter. The results are indicated in FIG. 2 wherein curve A represents the counts corresponding to beads incubated with immune complexes in a dissociating buffer (3 molar sodium thiocyanate) only. Similar results are obtained when instead of using 3 molar sodium thiocyanate as the dissociating buffer, 8 molar urea is employed.

Curve B represents the graph derived from the counts obtained when using immune complexes diluted in a phosphate buffered saline solution, a non-dissociating buffer.

Line C represents the background noise. The graph reveals the virtual insensitivity of the test when a non-dissociating buffer is employed. It is theorized that when using a non-dissociating buffer the antigen/antibodies remain in the form of immune complexes. Thus, when that buffered solution is brought in contact with the polystyrene beads, the antigens or antibodies are adsorbed by the polystyrene beads but in the form of immune complexes. Thus, for instance, the antigen sites which would normally be available for the $^{125}$I-labeled antibodies are already occupied by the antibodies of the immune complex. Only a few unoccupied sites remain available for the $^{125}$I-labeled antibodies. Thus, the presence of these antigens remains largely undetected, as vividly illustrated in FIG. 2.

It is evident from the results herein that not only does the process detect the presence of antigens or antibodies sequestered as an immune complex in a serum, but that such antigens or antibodies, as the case may be, are detectable in nanogram quantities, notwithstanding the copresence of other proteins. The process can readily be carried out using readily available materials. The process is useful for a wide variety of antigens and antibodies.

EXAMPLE 4

Example for detection of immune complexes in human serum specimens 250 ml=microliter serum samples from carriers of hepatitis B virus (HBV) or from healthy blood donors were mixed with a solution of polyethyleneglycol 6000 (PEG) (300 g/l) so that the final level of PEG was 5%. The precipitates, expected to contain immune complexes, were pelleted by centrifugation, the supernatants were aspirated and the pellets were dissolved in neutral (pH 6-8) saline (250 ml) and mixed with an equal volume of a 50% suspension of Staphylococci bearing protein A. After incubation at room temperature, the bacteria with the adsorbed immune complexes, were separated by centrifugation, washed with buffered saline (pH~7) and eluted with 3M NaSCN. HBsAg in the eluate was either detected by blotting on sheets of cellulose derivatives or after adsorption to polystyrene beads. (FIG. 2).

Detection of free antigen on the surface of the cellulose or plastic is performed in the manner of the preceding examples using radioactively labelled antibodies followed by incubation and detection of radio-labelled antibodies on the support. The results confirmed the existence of immune complexes in the original samples, not present in normal blood.

What is claimed is:

1. A process for determining the presence of an antigen or antibody in a sample wherein said antigen or antibody exists in the form of an immune complex which comprises:

A. contacting the immune complex originating from the sample suspected of containing immune complex with a dissociating buffer whereby said immune complex, if present, is dissociated into antigen and antibody;
   B. contacting a solid support which binds proteins with said dissociating buffer suspected of containing antigen or antibody and removing said buffer;
   C. washing said solid support;
   D. adding protein to fill unoccupied sites on said solid support;
   E. adding radioactively labeled or enzyme labeled antibody or antigen to said solid support, said labeled antibody or antigen corresponding to antigen or antibody on said solid support, incubating the resultant mass and washing the same;
   F. measuring the radioactivity or enzymatic activity associated with the solid support.

2. A process according to claim 1, wherein the solid support of step B is a derivatized paper or plastic material.

3. A process according to claim 2, wherein said solid support is a paper (cellulose) derivative.

4. A process according to claim 3, wherein said paper is a nitrocellulose paper.

5. A process according to claim 3, wherein said paper is a diazobenzyloxymethyl paper or a diazophenylthioether paper.

6. A process according to claim 2, wherein said solid support is a plastic material.

7. A process according to claim 6, wherein said plastic is a polystyrene.

8. A process according to claim 6, wherein said plastic is a polyvinyl material.

9. A process according to claim 6, wherein said plastic is a polyolefin.

10. A process according to claim 1, wherein the solid support of step B is a paper derivatized and step D is performed prior to step E.

11. A process according to claim 6, wherein steps D and E are performed simultaneously.

12. A process according to claim 1, wherein step E is performed using a radiolabeled antigen or antibody and step F is performed using radio-immunoassay or autoradiography.

13. A process according to claim 1, wherein step E is performed using an enzyme labeled antibody or antigen and step F is performed using an enzyme labeled immunoassay method.

14. A process according to claim 1, wherein prior to step A a mixture suspected of containing immune complex is brought in contact with a separating support which binds proteins whereby said immune complex, if present, is adsorbed to said separating support and thereby separated from materials with which it has been in admixture and thereafter the dissociating buffer is added to said separating support containing immune complex.

15. A process according to claim 14, wherein the sample suspected of containing immune complex is initially treated with a selective protein precipitating agent whereby immune complexes are precipitated if present. Precipitate is separated from supernatant material and the immune complex is taken up in solution by contacting the precipitate with a neutral, non-dissociating buffer prior to being brought in contact with said separating support.

16. A process according to claim 14, wherein said separating support comprises Staphylococci carrying proteint (A).

17. A process according to claim 15, wherein said separating support comprises Staphylococci carrying protein (A).

18. A process according to claim 1, wherein said buffer comprises an alkali or alkaline earth metal thiocyanate of pH 6-8.

19. A process according to claim 14, wherein said buffer comprises an alkali or alkaline earth metal thiocyanate of pH 6-8.

20. A process according to claim 15, wherein said buffer comprises an alkali or alkaline earth metal thiocyanate of pH 6-8.

21. A process according to claim 1, wherein said sample contains an immune complex of Hepatitis B (surface) antigen.

22. A process according to claim 14, wherein said sample contains an immune complex of Hepatitis B (surface) antigen.

23. A process according to claim 15, wherein said sample contains an immune complex of Hepatitis B (surface) antigen.

* * * * *